(12) United States Patent
Plantier et al.

(10) Patent No.: US 9,700,603 B2
(45) Date of Patent: Jul. 11, 2017

(54) USE OF ANTIDOTES TO COAGULATION INHIBITORS INDICATED IN THE PREVENTION OR TREATMENT OF THROMBOEMBOLIC PATHOLOGIES

(71) Applicants: LABORATOIRE FRANCAIS DU FRACTIONNEMENT ET DES BIOTECHNOLOGIES, Les Ulis (FR); Marc Samama, Chatillon (FR)

(72) Inventors: Jean-Luc Plantier, Croix (FR); Meyer-Michel Samama, Paris (FR)

(73) Assignee: LABORATOIRE FRANCAIS DU FRACTIONNEMENT ET DES BIOTECHNOLOGIES, Les Ulis (FR)

( * ) Notice: Subject to any disclaimer, the term of this patent is extended or adjusted under 35 U.S.C. 154(b) by 0 days.

(21) Appl. No.: 14/654,595

(22) PCT Filed: Jan. 8, 2014

(86) PCT No.: PCT/FR2014/050020
§ 371 (c)(1),
(2) Date: Jun. 22, 2015

(87) PCT Pub. No.: WO2014/108632
PCT Pub. Date: Jul. 17, 2014

(65) Prior Publication Data
US 2015/0343033 A1    Dec. 3, 2015

(30) Foreign Application Priority Data

Jan. 11, 2013   (FR) .................................. 13/50278

(51) Int. Cl.
*A61K 38/48*      (2006.01)
*A61K 31/5377*    (2006.01)
*C12Q 1/56*       (2006.01)
*A61K 38/36*      (2006.01)

(52) U.S. Cl.
CPC ...... *A61K 38/4846* (2013.01); *A61K 31/5377* (2013.01); *A61K 38/36* (2013.01); *C12Q 1/56* (2013.01); *C12Y 304/21006* (2013.01); *G01N 2333/96463* (2013.01)

(58) Field of Classification Search
CPC ....................................................... A61K 38/36
See application file for complete search history.

(56) References Cited

U.S. PATENT DOCUMENTS

| 6,376,515 B2 | 4/2002 | Zhu et al. |
| 6,835,739 B2 | 12/2004 | Zhu et al. |
| 8,455,441 B2 * | 6/2013 | Lu ...................... A61K 38/4826 |
| | | 424/185.1 |

FOREIGN PATENT DOCUMENTS

| EP | 0 700 684 A2 | 3/1996 |
| WO | 2008/145989 A1 | 12/2008 |
| WO | 2010/117729 A1 | 10/2010 |
| WO | 2011/008885 A1 | 1/2011 |

OTHER PUBLICATIONS

Ivanciu et al. Nature Biotechnology, 2011, 29(11):1028-1033.*
International Search Report, dated Apr. 4, 2014, from corresponding PCT application.
Genmin Lu et al., "Recombinant Antidote, for Reversal of Anticoagulation by Factor Xa Inhibitors", Blood, Nov. 1, 2008, p. 362, vol. 112, No. 11.
Elise S. Eerenberg et al., "Reversal of Rivaroxaban and Dabigatran by Prothrombin Complex Concentrate A Randomized, Placebo-Controlled, Crossover Study in Healthy Subjects", Circulation, Oct. 2011, pp. 1573-1579, vol. 124, No. 14.
Mark A. Crowther et al., "Bleeding risk and the management of bleeding complications in patients undergoing anticoagulant therapy: focus on new anticoagulant agents", Blood, Oct. 15, 2008, pp. 4871-4879, vol. 111, No. 10.

* cited by examiner

*Primary Examiner* — Bin Shen
(74) *Attorney, Agent, or Firm* — Young & Thompson

(57) ABSTRACT

The use of factor Xa in the prevention or treatment in a patient, in particular a human being or an animal, of haemorrhagic events induced by taking anticoagulants.

16 Claims, 10 Drawing Sheets

Figure 2:
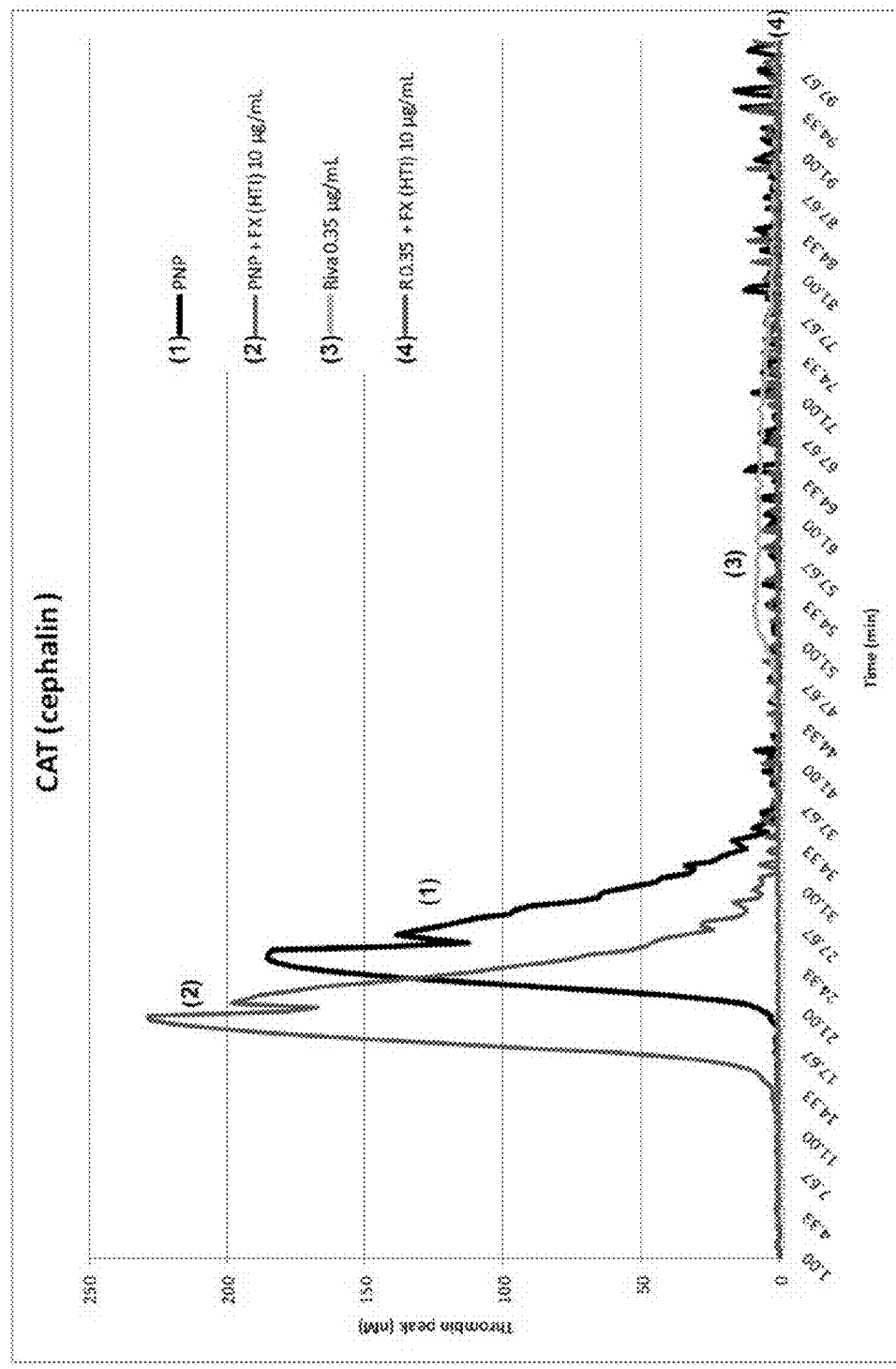

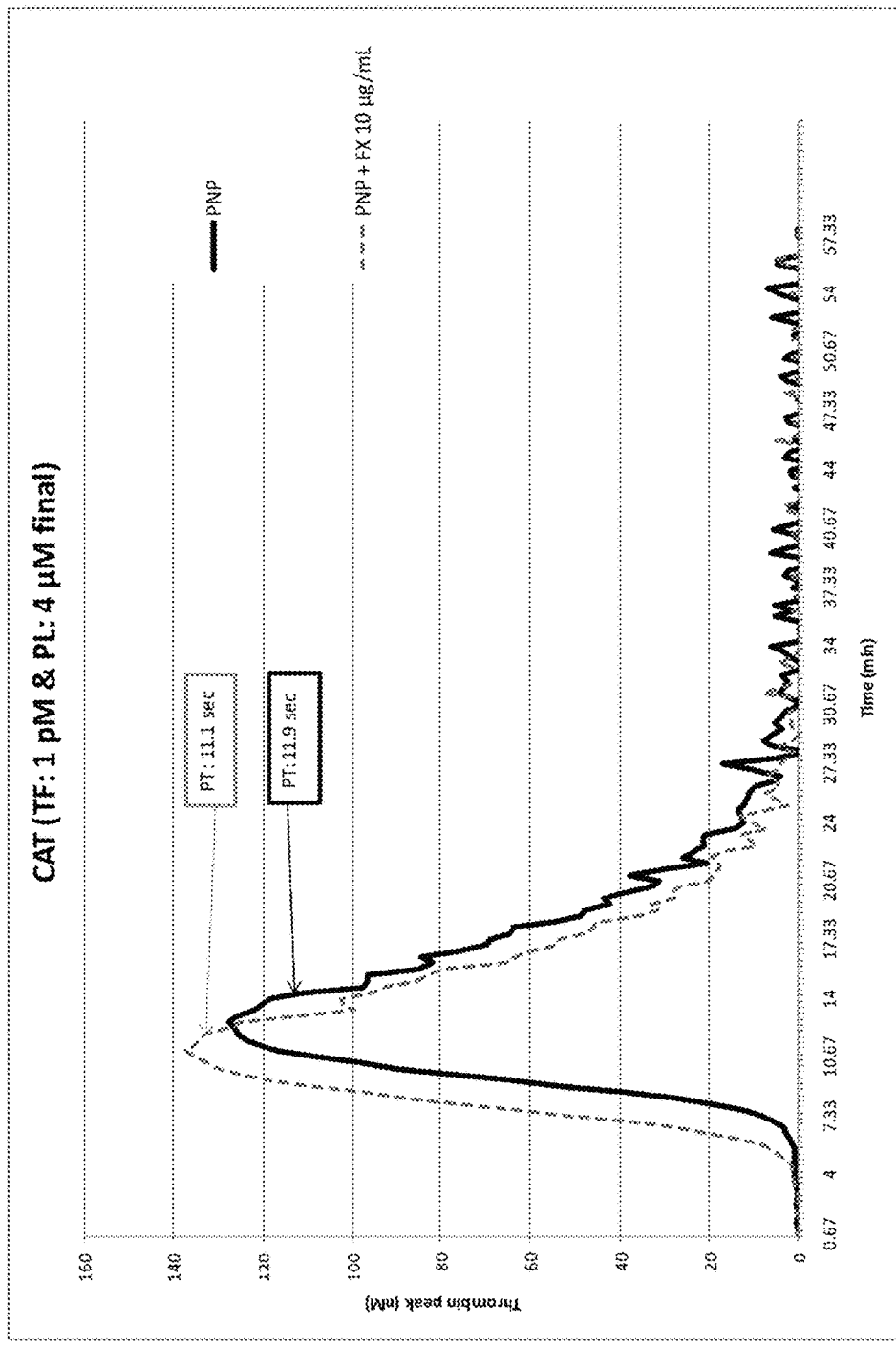
FIGURE 1-A

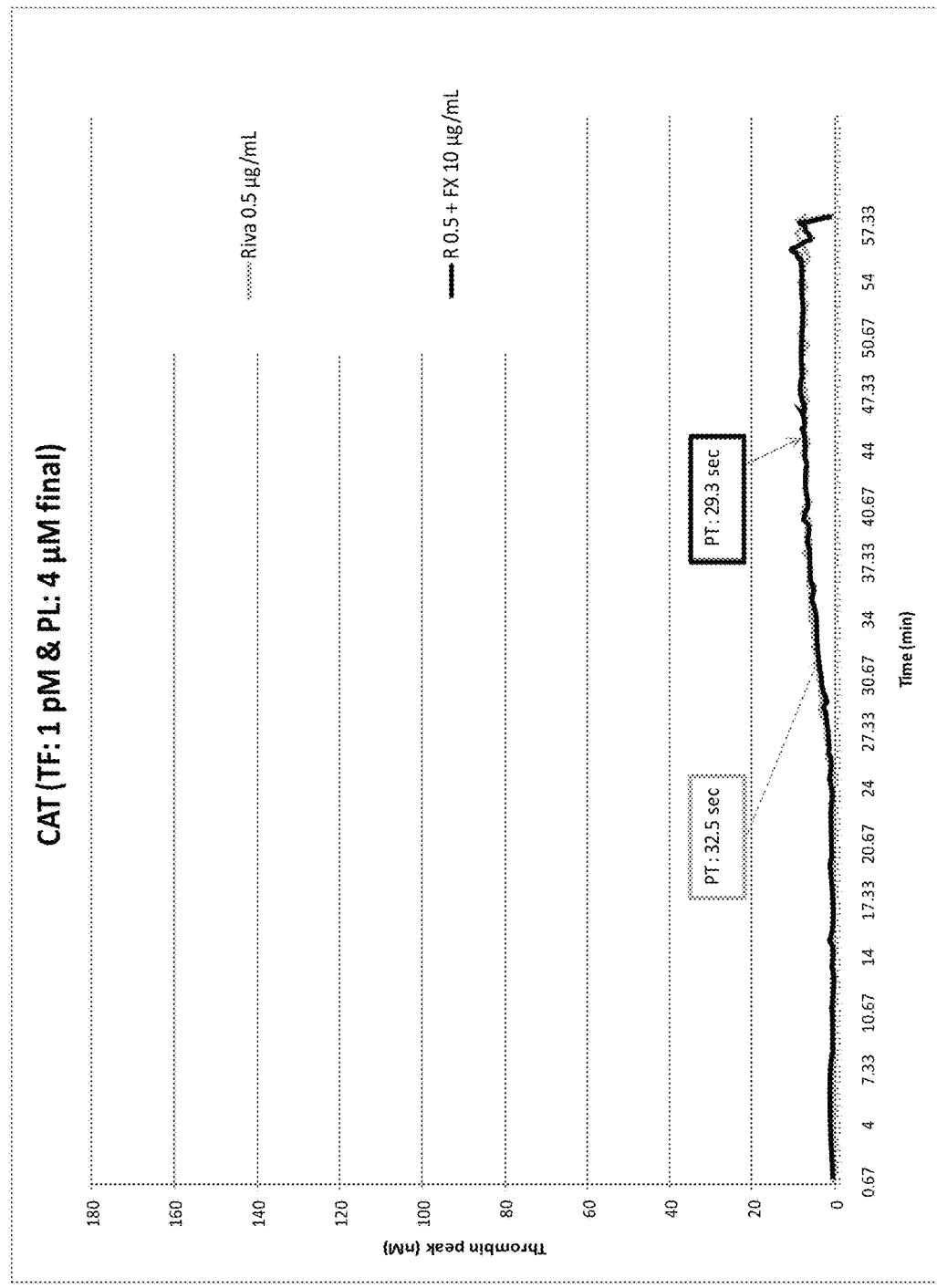
FIGURE 1-B

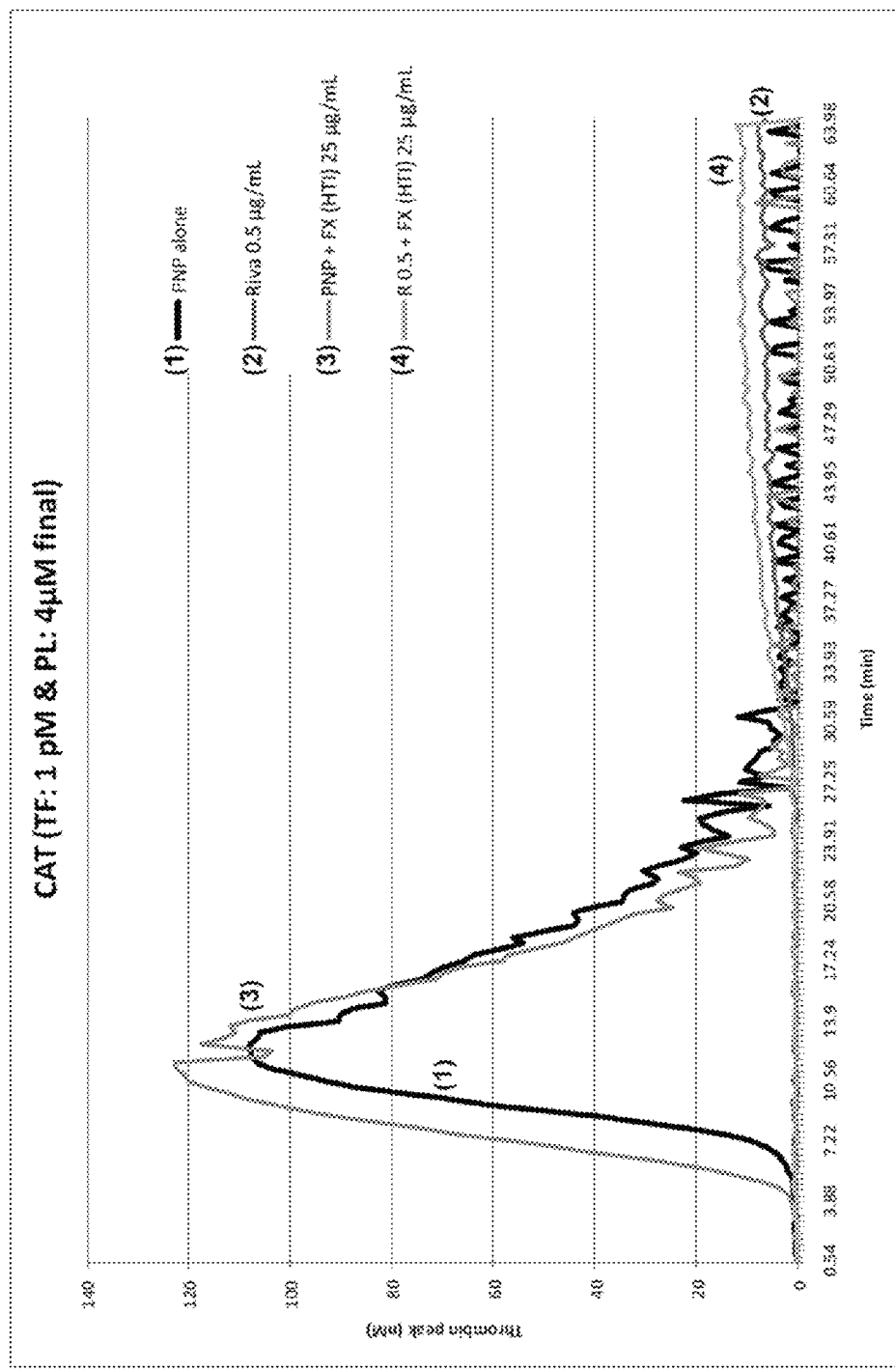
FIGURE 1-C

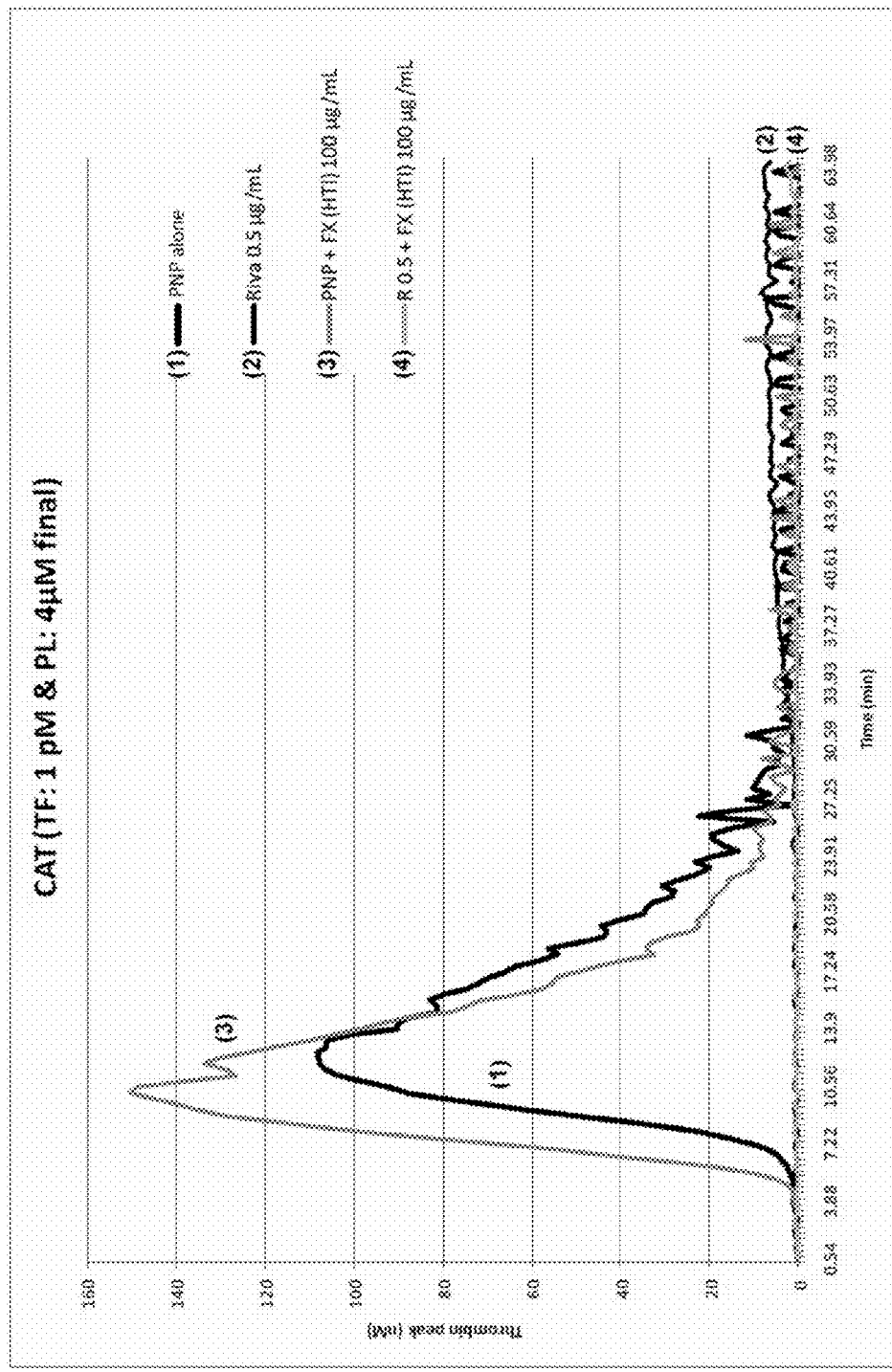
FIGURE 1-D

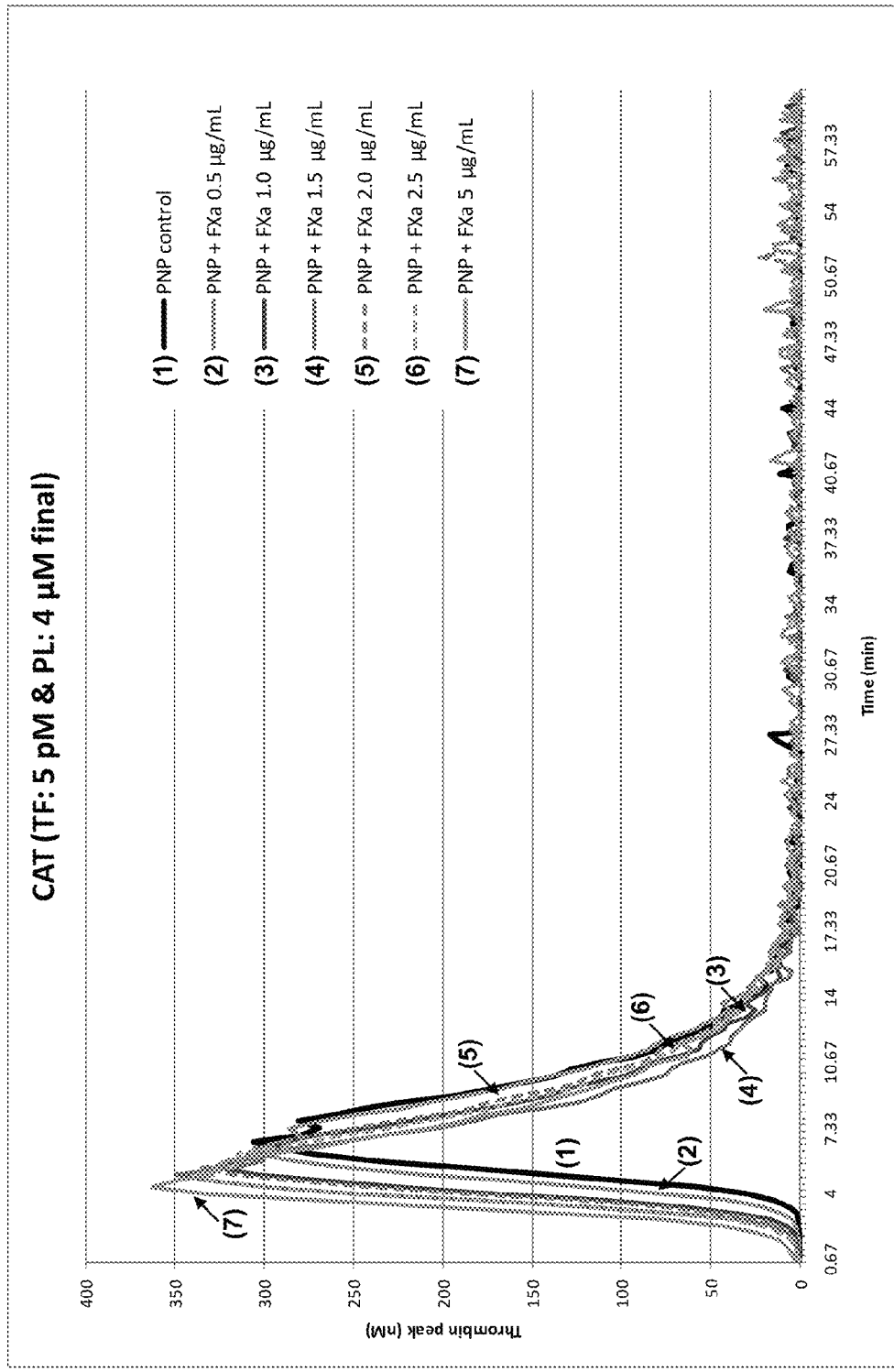
FIGURE 3-A

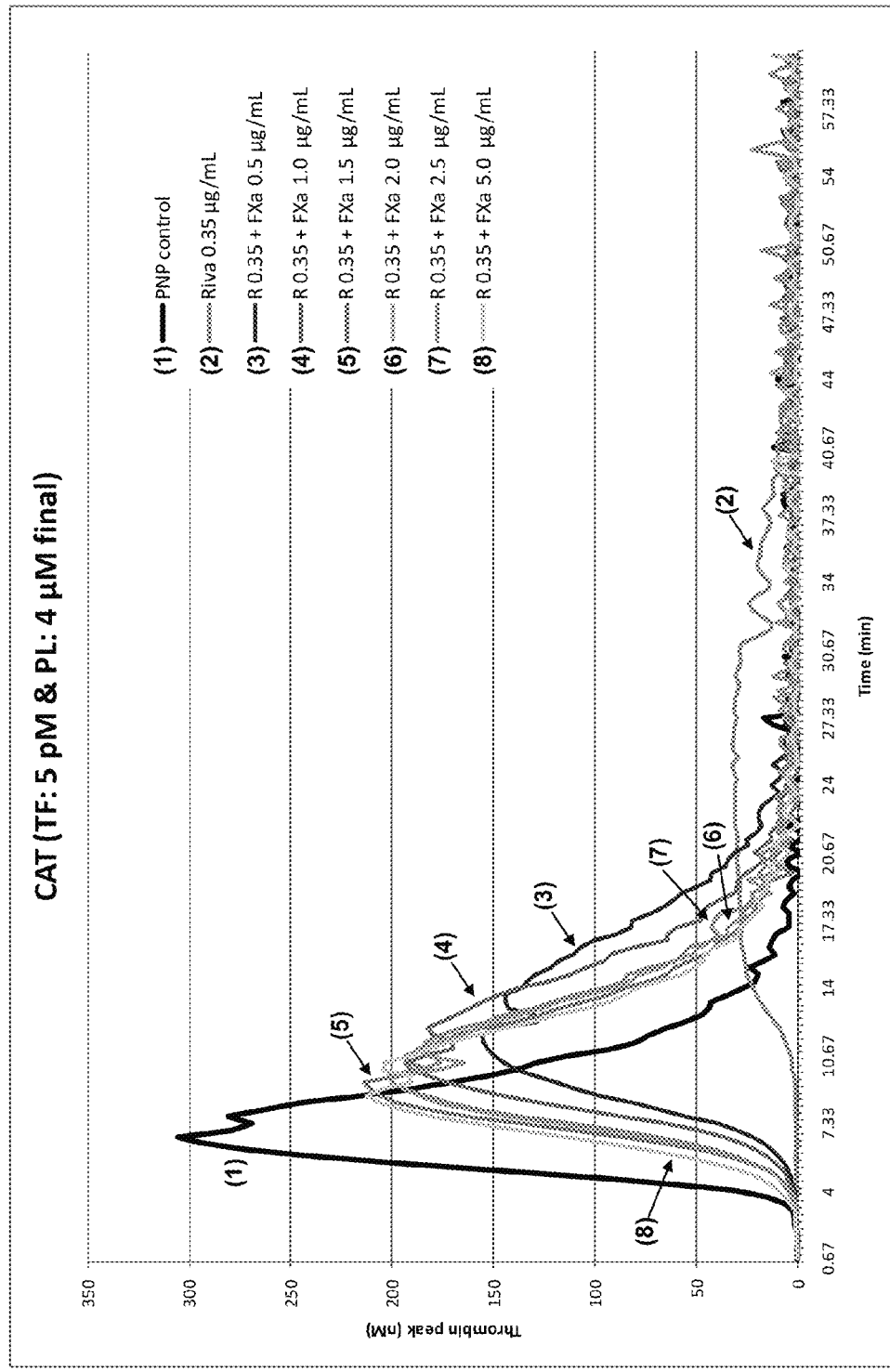
FIGURE 3-B

USE OF ANTIDOTES TO COAGULATION INHIBITORS INDICATED IN THE PREVENTION OR TREATMENT OF THROMBOEMBOLIC PATHOLOGIES

The present invention relates to the use of antidotes to coagulation inhibitors indicated in the prevention or treatment of thromboembolic pathologies.

Venous thrombosis constitutes a widespread pathology throughout the world which affects approximately 900,000 patients in the United States and 770,000 patients in Europe every year. In the prophylaxis of venous thromboembolic events, having available treatments that are effective and well tolerated with regard to haemorrhage, in particular in patients at risk, constitutes a public health need.

Venous thrombosis consists of the formation of a clot in a vein. It can be "superficial" when it affects the small veins situated between the skin and the muscles, or "deep" when it affects a larger vein. Deep thromboses are usually located in the lower limbs (legs, thighs, inguinal folds). Under the effect of different factors, the clot can become detached from the vein in which it is lodged, enter the bloodstream and cause a pulmonary embolism (obstruction of the pulmonary artery) which can be life-threatening or lead to significant after-effects.

Although the prevalence of venous thrombosis increases significantly with age, other risk factors associated with venous thrombosis have been identified. These are in particular hereditary or acquired coagulation diseases (deficiencies in antithrombin, C and S proteins and factor V Leiden, prothrombin mutation), obesity, cardiac insufficiency, confinement to bed following surgery or pregnancy, taking oral contraceptives combined with tobacco dependence. More generally, any period resulting in a slowing down of the blood circulation (venous stasis) promotes the appearance of small vascular lesions forming an area suitable for the development of thromboses.

The risk of venous thrombosis is particularly high in a patient having undergone major orthopaedic surgery on the lower limbs, in particular during a hip or knee replacement, or reduction of a femoral neck fracture. In order to prevent the occurrence of post-operative venous thrombosis, the clinician systematically uses anticoagulants.

Anticoagulants are divided into several categories depending on the target proteins of the coagulation cascade.

The vitamin K antagonists (VKAs), in particular the coumarins or 1,3-indandiones, target factors II, VII, IX and X of the coagulation cascade. These molecules, commonly used in situations where there is a major risk of clotting, require regular blood samples in order to check the INR (International Normalization Ratio). Given their ability to modify the circulating plasma proteins, the VKAs have a long half-life which makes their use somewhat inflexible.

Standard heparin (unfractionated: heparin, calciparine) and low-molecular-weight heparins (LMWHs) such as enoxaparin (Lovenox®), tinzaparin (Innohep®), bemiparin (Ivor®), nadroparin (Fraxiparine®), parnaparin (Flexum®), reviparin (Clivarine®) or deltaparin (Fragmin®) are glycosaminoglycans constituted by chains comprising alternating residues of D-Glucosamine and uronic acid. These compounds are capable of enhancing antithrombin activity and thus inhibiting activated factor X (FXa) and activated factor II (FIIa). The LMWHs also directly inhibit FXa, thus inhibiting the conversion of prothrombin to thrombin. Given their efficacy which is greater than that of unfractionated heparin and their fewer side effects in terms of thrombopaenia, the LMWHs are preferentially injected into patients.

More recently, novel oral anticoagulants have been developed. These are direct specific inhibitors of thrombin (dabigatran (Pradaxa®), hirudin) or of activated factor X (apixaban, betrixaban, edoxaban, otamixaban or rivaroxaban (Xarelto®)). These compounds are rapidly metabolized and reach a maximum plasma concentration in the 2 to 4 hours following their administration. Their efficacy is comparable to that of the LMWHs in the treatment of venous thrombosis following hip or knee surgery. However, use of these compounds is contra-indicated in patients suffering from a hepatic dysfunction or renal insufficiency.

Taking anticoagulants in the context of an anti-thrombotic treatment can give rise to the occurrence of haemorrhagic complications, which are rare but sometimes fatal. The speed of intervention is then decisive and the anticoagulants must be made to take effect as quickly as possible. The action of the VKAs can be reversed by conventional means such as vitamin K or plasma transfusion. However, the effects of vitamin K persist for several days, making its use difficult. As regards the LMWHs, protamine makes it possible to inhibit the anti-FIIa activity but only partially neutralizes the anti-FXa activity; only dialysis allows the complete removal of these compounds from the bloodstream, thus re-establishing the patient's natural coagulation ability. Haemodialysis can also be envisaged in the case of dagitraban but proves ineffective in the case of rivaroxaban. The use of prothrombin complex concentrate as an antidote to the anticoagulants was first envisaged in the mid-90s (EP 0 700 684 A2). More recently, the works of Eerenberg et al. have shown that these compounds make it possible to immediately and completely reverse the anticoagulant effect of rivaroxaban in healthy patients (Eerenberg et al., 2011, Circulation, 124, 1573-1579). Although the use of procoagulant molecules such as activated factor VII (FVIIa) can be envisaged, its weak procoagulant activity in the absence of its cofactor, tissue factor, limits the therapeutic benefit thereof.

The compound PRT4445, currently under development, constitutes the only therapeutic agent capable of binding and neutralizing all the direct and indirect inhibitors of activated factor X thus making it possible to restore normal haemostatic function (WO 2011/008885 A1). This compound is in fact a protein derived from FX or FXa in which the active site and/or the Gla domain have been invalidated, thus reducing the intrinsic procoagulant activity of these factors (WO 2010/117729 A1). Phase 1a clinical trials relating to the use of the compound PRT4445 as an antidote to betrixaban (U.S. Pat. No. 6,376,515 and U.S. Pat. No. 6,835,739) are imminent.

At present clinicians have no antidote to FXa inhibitors approved by the public health authorities. There is consequently a real need to identify therapeutic agents capable of rapidly reversing the anticoagulant effect of FXa inhibitors whilst not causing any risk of thrombosis.

The purpose of the present invention is to propose a method for preventing and treating a haemorrhagic event after taking anticoagulants.

Another purpose of the present invention is to restore normal haemostatic function during the occurrence of a haemorrhagic event in a patient undergoing treatment with anticoagulants.

Yet another purpose of the present invention is to provide an antidote to the inhibitors of activated factor X (FXa).

The present invention relates to factor Xa (FXa) for the use thereof in the prevention or treatment in a patient, in particular a human or an animal, of haemorrhagic events induced by taking anticoagulants.

The invention is based on the unexpected finding that factor Xa is capable of rapidly reversing the anticoagulant effect of the anticoagulants, without inducing any risk of thrombosis, and restoring the "normal" haemostatic function during the occurrence of a haemorrhagic event after taking anticoagulants.

By "factor Xa", also called FXa or also activated factor X, is meant a serine protease of the coagulation cascade, obtained from inactive factor X (Butenas & Mann, Biochemistry (Moscow), 2002, 67(1), 3-12). The proteolysis of FX to FXa is carried out either by the tenase complex (activated factor IX (FIXa) and its cofactor, activated factor VIII (FVIIIa) in the presence of calcium and phospholipids) or by the activated factor VII (FVIIa)/tissue Factor complex in the presence of calcium. FXa forms, with activated factor V (FVa), the prothrombinase complex which catalyzes the conversion of prothrombin (factor II, FII) to thrombin (activated factor II, FIIa). The thrombin catalyzes the conversion of fibrinogen to fibrin which is responsible for the formation of the blood clot. FXa is characterized by a procoagulant activity. FXa occupies a central place in the intrinsic and extrinsic coagulation pathways.

Factor Xa serves as an antidote to the anticoagulants. By "antidote", is meant the molecules, and in particular FXa, capable of neutralizing or reversing all or part of the anticoagulant activity of the anticoagulants. This effect must be able to occur within a more or less short period of time, in relation to the location and the magnitude of the haemorrhagic event in order to slow down, attenuate or completely stop this haemorrhagic event. The anticoagulant activity of the anticoagulants can be measured by overall coagulometric tests (Quick time (PT), activated cephalin time (aPTT)). In their presence, there is a reduction in the INR (International Normalized Ratio). The measurement of their effects can also be envisaged by coagulation tests which measure thrombin generation (TGT).

By "haemorrhagic events", is meant visible or invisible bleeds resulting from the rupture of blood vessels, in particular of deep or superficial veins, or venules. The extent of visible bleeds is assessed by simple observation. By contrast, the following signs can reveal the existence of invisible bleeds: asthaenia, dyspnoea, pallor, headaches resistant to the usual treatments, dizzy spells. Haemorrhagic events within the meaning of the present invention are an adverse effect of the misuse of anticoagulants. The severity of the bleeds depends on their location and their intensity and is assessed by the need for a transfusion or the extent to which it is life-threatening to the patient. Beside intracranial haemorrhagic strokes, the clinical forms vary greatly and can be presented as haemorrhages which are externalized or not (digestive haemorrhage, retroperitoneal haematoma, urological and gynaecological bleeds, haematoma of the soft tissues, epistaxis, haemoptysis, gingivorrhagia etc.). In the case of the least severe forms, the haemorrhagic events can lead to anaemia.

By "anticoagulants", is meant the compounds capable of inhibiting the formation of the blood clot and prolonging the coagulometric tests (aPTT and PT). The limitation of the formation of thrombin can also be assessed in TGT. The anticoagulants can be identified according to their pharmacological target. Thus a distinction is made between the vitamin K antagonists, unfractionated low-molecular-weight heparins, anti-tissue factor antibodies, the specific, direct or indirect inhibitors of factors IXa, Xa, XIa, XIIa or VIIa. The anticoagulants are administered to a patient, alone or in combination in one dose and according to a dosage regimen making it possible to prevent or treat clotting, thus reducing the risk of thrombosis.

According to a particular embodiment, in the use of factor Xa according to the present invention, the anticoagulants are low-molecular-weight heparins.

By "low-molecular-weight heparins", also called LMWHs, is meant the heparins resulting from the cleavage of the unfractionated heparin (Mousa ITS, Methods Mol. Biol., 2010, 663, 109-132). These anti-thrombotic compounds are administered by intravenous route, and their concentrations of use are expressed in international anti-FXa units even if their efficacy is not limited to this anti-FXa activity. The LMWHs have a longer half-life than the unfractionated heparins and have an interaction with the platelets which is less than that of the unfractionated heparins. The LMWHs have a molecular mass which varies from 4000 to 6000 Da. The low-molecular-weight heparins commonly used are enoxaparin (Lovenox®), tinzaparin (Innohep®), bemiparin) (Ivor®), nadroparin (Fraxiparine®), parnaparin (Flexum®), reviparin (Clivarine®), certoparin (Sandoparine®) or deltaparin (Fragmin®). The LMWHs are used preventively following surgery on a lower limb or when long-term immobilization is obligatory. By long-term immobilization is meant keeping the patient in bed for a period which varies from 3 days to several weeks.

According to a more particular embodiment, in the use of factor Xa according to the present invention, the low-molecular-weight heparins are selected from bemiparin, certoparin, deltaparin, enoxaparin, nadroparin, parnaparin, reviparin or tinzaparin.

According to another embodiment, in the use of factor Xa according to the present invention, the anticoagulants are specific inhibitors of factor Xa.

By "specific inhibitors of factor Xa", is meant the compounds capable of inhibiting, directly or indirectly, the procoagulant activity of FXa which consists of the conversion of prothrombin to thrombin in vitro, and/or ex vivo, and/or in vivo. The FXa inhibitors can be classified as inhibitors of a peptide nature, extracted and purified or obtained by genetic engineering or as inhibitors of a non-peptide nature obtained by chemical synthesis (Kher et al., 1998, La Lettre du pharmacologue, 12(6), 222-226). The inhibitors which block the active site of FXa are called direct inhibitors whereas the inhibitors which act by binding and catalyzing the effect of antithrombin vis-à-vis FXa are called indirect inhibitors. Examples of direct peptide inhibitors of FXa include, without this restricting the scope of the invention, TAP (tick anticoagulant peptide) extracted from tick saliva, antistasin extracted from the salivary glands of the leech *Haementeria officinalis*, ACAP (*ancylostoma caninum* anticoagulant peptide) isolated from the hookworm or its recombinant forms r Ac AP5, r Ac AP2 (also called NAP-5) or also FXa I (factor Xa inhibitor) extracted from the saliva of the leech *Hirudo medicinalis* or the recombinant protein corresponding thereto, called Yagin. The direct non-peptide inhibitors of FXa include DX 9065a, LY517717 and the xabans (eribaxaban, apixaban, betrixaban, edoxaban, otamixaban, rivaroxaban). The LMWHs, the oligosaccharides fondaparinux or idraparinux and the heparinoids (danaparoid, sulodexide, dermatan sulphate) constitute examples of indirect inhibitors of FXa.

In this particular embodiment, FXa constitutes the antidote to the specific inhibitors of FXa. The catalytic structure of FXa used according to the present invention allows binding to the specific inhibitors of FXa. The use of factor Xa as an antidote to FXa inhibitors allows the titration of these inhibitors. In the use of FXa as an antidote according to the present invention, the inhibitory activity of the specific inhibitors of FXa is reduced by at least approximately 10%, 20%, 30%, 40%, 50%, 60%, 70%, 80%, 90% or 100%. The reduction in the inhibitory activity of the anti-Xa is measured by the return of a functional activity of FXa or an increase in the procoagulant activity in the plasma. These activities can be measured using chromogenic measurement (cleavage of peptide specific to FXa or thrombin), chronometric measurement (aPTT, PT, increase in INR) or using overall coagulation measurement tests (measurement of thrombin generation time, TGT).

According to another particular embodiment, in the use of factor Xa according to the present invention, the anticoagulants are selected from the group constituted by the low-molecular-weight heparins, the oligosaccharides fondaparinux or idraparinux and the specific inhibitors of factor Xa.

According to yet another particular embodiment, in the use of factor Xa according to the present invention, the anticoagulants are the oligosaccharides fondaparinux or idraparinux.

According to yet another particular embodiment, in the use of factor Xa according to the present invention, the oligosaccharide is fondaparinux.

According to another more particular embodiment, in the use of factor Xa according to the present invention, the specific inhibitors of factor Xa are selected from apixaban, betrixaban, edoxaban, otamixaban or rivaroxaban.

According to another embodiment, in the use of factor Xa according to the invention, factor Xa restores the procoagulant activity without the latter exceeding the basal level of the procoagulant activity measured in a group of healthy patients.

By "procoagulant activity", is meant the catalytic activity of FXa which consists of cleaving prothrombin to thrombin. The term "prothrombin activation" is then used. The catalytic activity of FXa is similar to the catalytic activity of prothrombinase, a protein complex which contains not only FXa but also FVa.

By "basal level", is meant the level of FXa in a patient or in a group of healthy patients. Each patient has his own basal level of FXa which makes it possible for him to maintain an equilibrium in terms of coagulation. This basal level, close to zero under normal physiological conditions, can vary from one individual to another, in particular depending on the basal level of FX present in the blood.

By "patients", is meant any mammal, human or animal. In the context of the present invention, the patients have received at least one specific inhibitor of factor Xa.

By "healthy patients", is meant a group of patients who have no apparent pathology and are not undergoing treatment with specific inhibitors of factor Xa, i.e. having received no treatment with any one of the specific inhibitors of FXa. The benefit of carrying out the measurement of the FXa level in several healthy patients is being able to determine an average thereof which serves as a reference value. The comparison of this average reference value of FXa procoagulant activity with that of a patient undergoing treatment with inhibitors of FXa and receiving FXa as an antidote makes it possible to monitor the therapeutic effect of the antidote.

According to a particular embodiment, factor Xa for the use thereof according to the invention, is a native protein isolated from plasma or a recombinant protein.

By "native protein isolated from plasma", is meant FX found in the natural state in the plasma/serum of patients, which has undergone a purification step allowing it to be isolated from its natural matrix. The in vitro or ex vivo activation of FX thus isolated leads to the obtaining of FXa which has the ability to activate prothrombin.

By "recombinant protein", is meant a protein prepared, expressed, isolated, purified by genetic engineering. Recombinant DNA technology makes it possible to insert a polynucleotide sequence coding either for FXa, or for FX, into a host cell and thus produce the polypeptide of interest, i.e. FXa or FX which can be activated after cell production. It is also possible to modify the polynucleotide sequence coding for FX by inserting one or more intracellular cleavage sequences which will make it possible to directly obtain FXa. The recombinant protein FXa also has the ability to activate prothrombin.

According to a particular embodiment, factor Xa for the use thereof according to the invention, has improved properties with respect to native factor Xa isolated from plasma. This means that the gene and/or protein of factor Xa is modified in order to improve one or more of its biological properties with respect to native factor Xa isolated from plasma. In particular, factor Xa can have improved affinity vis-à-vis the therapeutic inhibitors of FXa, and/or improved ability to bind to its cofactor, activated coagulation factor V, and/or improved prothrombin activation properties, with respect to native factor Xa isolated from plasma.

According to a particular embodiment, factor Xa for the use thereof according to the invention, has an increased circulating half-life with respect to native factor Xa isolated from plasma. This means that the gene and/or protein of factor Xa is modified in order to increase its circulating half-life. By "half-life", is meant the period of time during which a protein is capable of performing its biological function. The shorter the half-life the more labile the protein. Conversely, the longer the half-life of a protein, the more stable the protein. Increasing the half-life of a protein is equivalent to increasing its stability in the bloodstream.

In fact, recent data suggest that FXa used as a procoagulant in haemophilic mice does not have a half-life sufficient to allow long-lasting restoration of the coagulation ability (Invanciu et al., 2011, Nature Biotechnology, 29(11), 1028-1035). Used in vitro in healthy plasma, FXa has the ability to normalize the failure of thrombin generation induced by rivaroxaban. However, this ability could be altered in vivo.

The activity of FXa could be supported by different chemical modification techniques such as, for example, and without limitation of the method, pegylation, or by the generation of mutated molecules that are less sensitive to the action of plasmatic inhibitors such as antithrombin for example, or by the use of chimeric molecules which would make it possible to increase the half-life, such as, for example and without being limited to their use alone, the fusion of factor Xa to albumin or to the crystallizable fragment of antibodies.

The present invention also relates to a method for monitoring in vitro or ex-vivo the occurrence of haemorrhagic events induced by taking specific inhibitors of factor Xa comprising the following steps:

a) analytical measurement of the blood coagulation markers in a biological sample originating from a patient receiving a specific inhibitor of factor Xa in order to obtain numerical values that can be assigned to each of the abovementioned markers, b) determination of the risk of haemorrhage from the numerical values established in step a), c) determination of a suitable quantity of factor Xa to be administered to said patient receiving a specific inhibitor of factor Xa.

By "analytical measurement", is meant the determination of the concentration or level of each of the coagulation markers. The determination of these concentrations is carried out in vitro or ex-vivo using diagnostic kits. The numerical values obtained are specific to each of the patients receiving a specific inhibitor of factor Xa.

By "coagulation markers", is meant coagulation time values established by measurement of the aPTT, PT or establishment of the INR.

By "biological sample", is meant a liquid fraction selected from the group constituted by blood, serum or plasma.

By "risk of haemorrhage", is meant the presumption of bleeding in a patient having received at least one inhibitor of FXa. The assessment of the risk of haemorrhage can be carried out starting from the coagulation markers alone or taken into consideration with analyses of medical imaging allowing the visualization of the haemorrhagic areas. Thrombin generation of less than 50% of normal leads to a risk of haemorrhage (Van Veen et al. British J Haematol., 2008, 142, 889-903).

Determination of the risk of haemorrhage is carried out in particular by comparison of the numerical values determined for each of the markers in a patient receiving a specific inhibitor of FXa with numerical reference values. These numerical reference values can correspond either to the average of the numerical values obtained in healthy subjects for each of the markers, or be fixed or calculated with respect to international standards.

By "suitable quantity", is meant the quantity of FXa that is effective in achieving the intended therapeutic result. In the context of the present invention, the therapeutic aim consists of the partial or total reduction of the haemorrhage. The assessment of the therapeutic result can be based on the clinical presentation of the patient or on any other indicator of a biological nature. In the context of the present invention, the biological indicators are in particular the neutralization of the FXa inhibitor administered to the patient, the reversal of the anticoagulant activity of the FXa inhibitor, the removal of the FXa inhibitor from the patient's plasma, the restoration of haemostasis and the reduction or cessation of bleeding. The effective quantity of FXa can vary depending on the type and dose of FXa inhibitor administered to the patient, the morphology and age of the patient as well as of the method of administration of FXa. The management of these different parameters is well known to a person skilled in the art.

The present invention also relates to a pharmaceutical composition comprising factor Xa and an inhibitor of factor Xa as a combination product for use, separately or spread over time, in the prevention or treatment in a patient, in particular a human being or an animal, of venous thromboembolic events, for example following orthopaedic surgery on the hip and/or the knee.

By "pharmaceutical composition", is meant the combination of an active compound, in particular FXa, with at least one pharmaceutically acceptable compound making the composition suitable for administration to a patient.

By "combination product", is meant a product containing at least two compounds A and B which can be administered jointly in one dose, or product A is administered then product B is administered immediately after, or product A is administered then product B is administered several minutes, hours, days later. In the context of the present invention, the combination product comprises the specific inhibitor of FXa (product A) and FXa (product B).

By "venous thromboembolic event", is meant the formation of a clot capable of obstructing the vessel in which it is formed or capable of leaving the vessel in which it is formed, to be found in the bloodstream. The formation of the blood clot is also called thrombosis. The frequency of occurrence of thromboembolic events increases when the patient undergoes prolonged immobilization. Orthopaedic surgery on the lower limbs (hip, leg, knee) generally requires prophylactic treatment of the patient with anticoagulants in order to prevent the occurrence of thrombosis.

According to a particular embodiment, in the pharmaceutical composition according to the present invention, the concentration of factor Xa varies from 0.01 ng/ml to 2 µg/ml or from 10 µg/ml to 2 µg/ml.

A defined volume of pharmaceutical composition according to the present invention makes it possible to define unit doses of FXa that can be administered to a patient receiving a specific inhibitor of FXa.

By "unit dose", is meant the specific quantity of FXa that can be administered to a patient in one dose. The unit dose is the appropriate presentation of a defined quantity of FXa in a single-dose container, intended for administration to a patient.

The present invention also relates to a method for preventing or treating haemorrhagic events induced by taking anticoagulants, in a mammal, in particular a human, comprising a step of administration of factor Xa to said mammal, in particular a human, in a sufficient quantity making it possible to restore basal procoagulant activity.

This makes it possible to restore normal coagulation in a patient having received the antidote, but without the risk of causing a thrombosis. The aim is to stop the occurrence of a haemorrhage in a patient having received at least one anticoagulant.

According to a particular embodiment, in the method according to the present invention, the anticoagulants are specific inhibitors of factor Xa.

According to another more particular embodiment, in the method according to the present invention, the specific inhibitors of factor Xa are selected from apixaban, betrixaban, edoxaban, otamixaban or rivaroxaban.

According to another even more particular embodiment, in the method according to the present invention, factor Xa is administered to a mammal, in particular a human, during or after taking specific inhibitors of factor Xa.

The following figures and examples serve to illustrate the present invention but should in no way serve to restrict its scope.

CAPTIONS TO THE FIGURES

FIG. 1-A: Thrombinogram obtained from the addition of 10 µg/mL of FX to a normal plasma pool following activation with tissue factor:
  on the x-axis: time (in minutes)
  on the y-axis: the maximum concentration of thrombin observed (in nM)
The normal plasma pool sample is represented by the black curve (PT=11.9 seconds).
Factor X was added at a rate of 10 µg/mL (dotted grey curve) to the normal plasma pool sample (PT=11.1 seconds).

FIG. 1-B: Thrombinogram obtained from the addition of 10 µg/mL of FX to a plasma pool overloaded with 0.5 µg/mL of rivaroxaban following activation with tissue factor:
  on the x-axis: time (in minutes)
  on the y-axis: the maximum concentration of thrombin observed (in nM)

The plasma pool sample overloaded with 0.5 μg/mL of rivaroxaban is represented by the grey curve (PT=32.5 seconds).
Factor X was added at a rate of 10 μg/mL (black curve) to the sample overloaded with 0.5 μg/mL of rivaroxaban (PT=29.3 seconds).

FIG. 1-C: Thrombinogram obtained from the addition of 25 μg/mL of FX to a normal plasma pool overloaded with 0.5 μg/mL of rivaroxaban following activation with tissue factor:
  on the x-axis: time (in minutes)
  on the y-axis: the maximum concentration of thrombin observed (in nM)
The normal plasma pool sample is represented by the black curve (1).
The normal plasma pool sample overloaded with 0.5 μg/mL of rivaroxaban is represented by the curve (2).
Factor X was added at a rate of 25 μg/mL to the normal plasma pool sample (curve (3)) and to the normal plasma pool sample overloaded with 0.5 μg/mL of rivaroxaban (curve (4)).

FIG. 1-D: Thrombinogram obtained from the addition of 100 μg/mL of FX to a normal plasma pool overloaded with 0.5 μg/mL of rivaroxaban following activation with tissue factor:
  on the x-axis: time (in minutes)
  on the y-axis: the maximum concentration of thrombin observed (in nM)
The normal plasma pool sample is represented by the thick black curve (1).
The normal plasma pool sample overloaded with 0.5 μg/mL of rivaroxaban is represented by the thin black curve (2).
Factor X was added at a rate of 100 μg/mL to the normal plasma pool sample (grey curve (3)) and to the normal plasma pool sample overloaded with 0.5 μg/mL of rivaroxaban (light grey curve (4)).

FIG. 2: Thrombinogram obtained from the addition of 10 μg/mL of FX to a normal plasma pool overloaded with 0.35 μg/mL of rivaroxaban following induction with cephalin:
  on the x-axis: time (in minutes)
  on the y-axis: the maximum concentration of thrombin observed (in nM)
The normal plasma pool sample is represented by the black curve (1).
The normal plasma pool sample overloaded with 0.35 μg/mL of rivaroxaban is represented by the curve (3).
Factor X was added at a rate of 10 μg/mL to the normal plasma pool sample (curve (2)) and to the normal plasma pool sample overloaded with 0.35 μg/mL of rivaroxaban (curve (4)).

FIG. 3-A: Thrombinogram obtained from the addition of increasing doses of FXa to a normal plasma pool:
  on the x-axis: time (in minutes)
  on the y-axis: the maximum concentration of thrombin observed (in nM)
The normal plasma pool sample is represented by the black curve (1).
Factor Xa was added at a rate of 0.5 μg/mL (curve (2)), 1.0 μg/mL (curve (3)), 1.5 μg/mL (curve (4)), 2.0 μg/mL (curve (5)), 2.5 μg/mL (curve (6)), 5.0 μg/mL (curve (7)) to the normal plasma pool sample.

FIG. 3-B: Thrombinogram obtained from the addition of increasing doses of FXa to a normal plasma pool overloaded with 0.35 μg/mL of rivaroxaban:
  on the x-axis: time (in minutes)
  on the y-axis: the maximum concentration of thrombin observed (in nM)
The normal plasma pool sample is represented by the black curve (1).
0.35 μg/mL of rivaroxaban was added to the normal plasma pool sample (curve (2)).
Factor Xa was added at a rate of 0.5 μg/mL (curve (3)), 1.0 μg/mL (curve (4)), 1.5 μg/mL (curve (5)), 2.0 μg/mL (curve (6)), 2.5 μg/mL (curve (7)), 5.0 μg/mL (curve (8)) to the normal plasma pool sample overloaded with 0.35 μg/mL of rivaroxaban.

Figure 4:
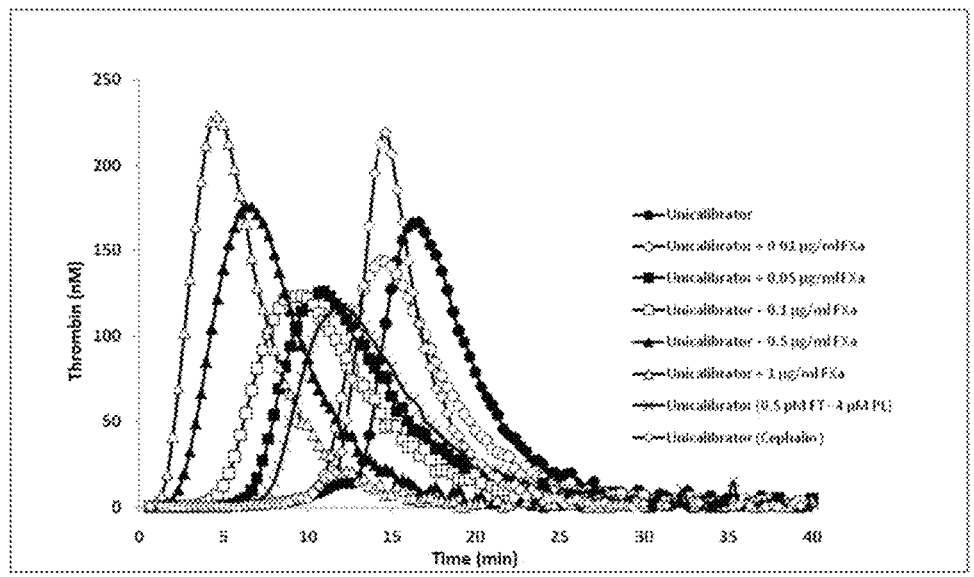

FIG. 4: Thrombinograms obtained from the addition of 0.01 to 1 μg/mL of activated FX to a normal plasma pool without activation:
  on the x-axis: time (in minutes)
  on the y-axis: the maximum concentration of thrombin observed (in nM)
The normal plasma pool sample is represented by the curve ●. The effect of the concentrations of FXa added to normal plasma is represented by the following curves: 0.01 μg/ml (○); 0.05 μg/ml (■); 0.1 μg/ml (□); 0.5 μg/ml (▲) and 1 μg/ml (Δ). The controls illustrating thrombin generation following the induction of coagulation either by tissue factor/phospholipids (x) or by cephalin (◊) are indicated.

Figure 5:
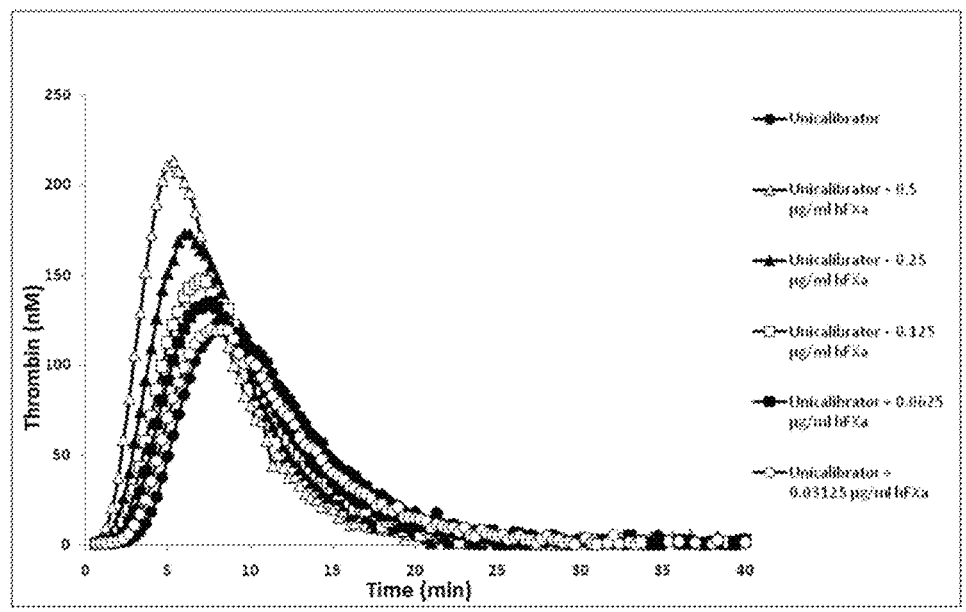

FIG. 5: Thrombinograms obtained from the addition of 0.03 to 0.5 μg/mL of activated FX to a normal plasma pool following activation with tissue factor:
  on the x-axis: time (in minutes)
  on the y-axis: the maximum concentration of thrombin observed (in nM)
The normal plasma pool sample is represented by the curve ●. The effect of the concentrations of FXa added to normal plasma is represented by the following curves: 0.0312 μg/ml (○); 0.0625 μg/ml (■); 0.125 μg/ml (□); 0.25 μg/ml (▲) and 0.5 μg/ml (Δ).

Figure 6:
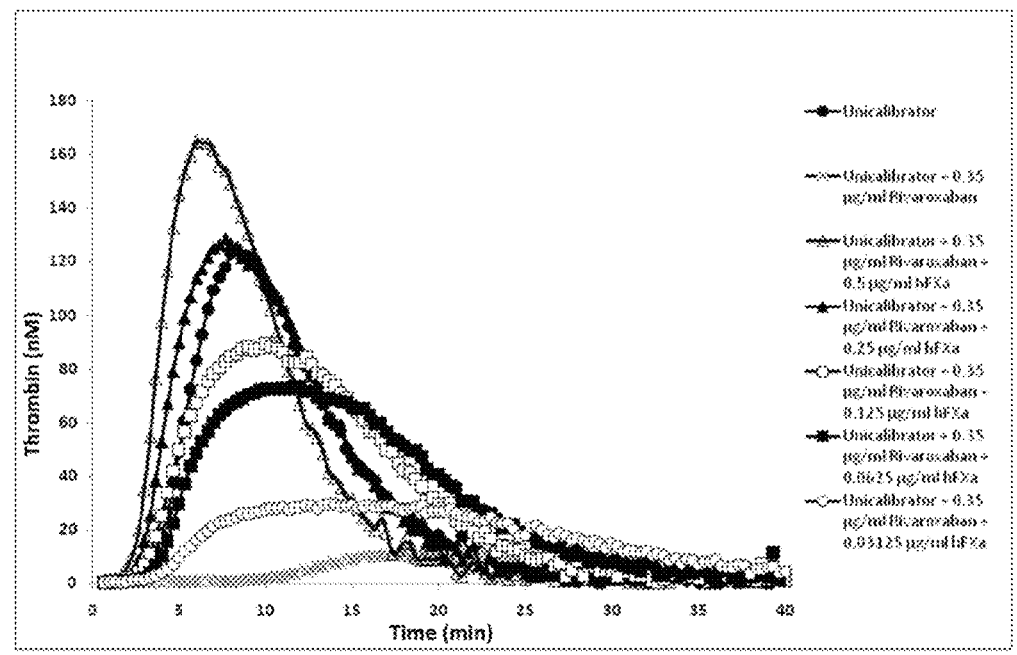

FIG. 6: Thrombinograms obtained from the addition of 0.03 to 0.5 μg/mL of activated FX to a normal plasma pool in the presence of Rivaroxaban (0.35 μg/ml) following activation with tissue factor:
  on the x-axis: time (in minutes)
  on the y-axis: the maximum concentration of thrombin observed (in nM)
The normal plasma pool sample without Rivaroxaban (0.35 μg/ml) is represented by the curve ●. The same plasma activated under the same conditions but in the presence of Rivaroxaban (0.35 μg/ml) is represented by the curve x. The effect of the concentrations of FXa added to normal plasma in the presence of Rivaroxaban (0.35 μg/ml) is represented by the following curves: 0.0312 μg/ml (○); 0.0625 μg/ml (■); 0.125 μg/ml (□); 0.25 μg/ml (▲) and 0.5 μg/ml (Δ).

Figure 7:
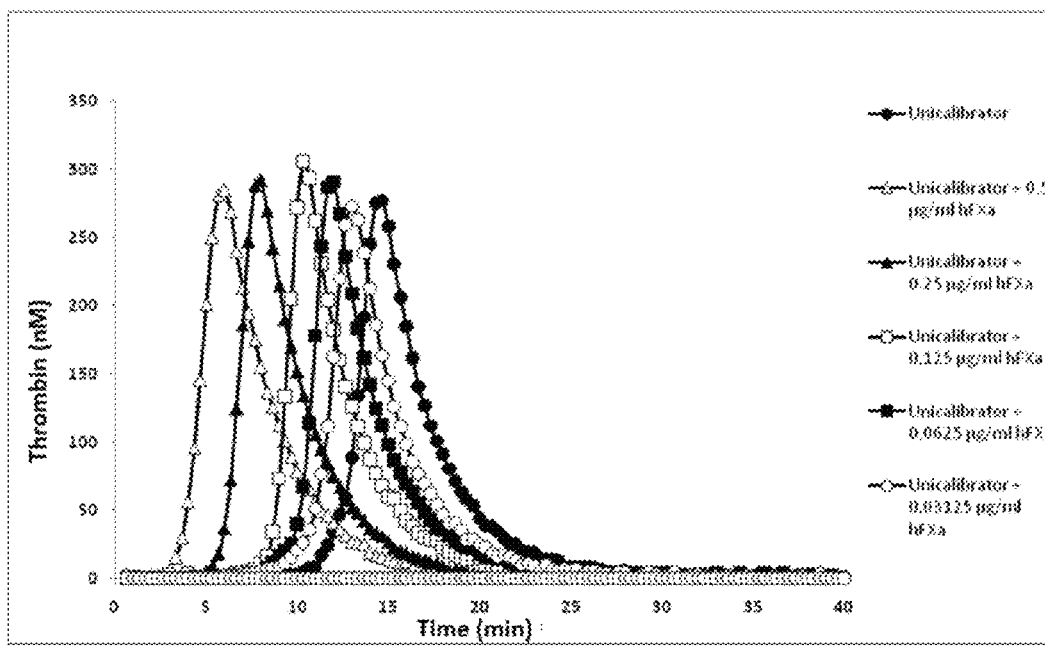

FIG. 7: Thrombinograms obtained from the addition of 0.03 to 0.5 μg/mL of activated FX to a normal plasma pool following activation with cephalin:
  on the x-axis: time (in minutes)
  on the y-axis: the maximum concentration of thrombin observed (in nM)
The normal plasma pool sample is represented by the curve ●. The effect of the concentrations of FXa added to normal plasma is represented by the following curves: 0.0312 μg/ml (○); 0.0625 μg/ml (■); 0.125 μg/ml (□); 0.25 μg/ml (▲) and 0.5 μg/ml (Δ).

Figure 8:
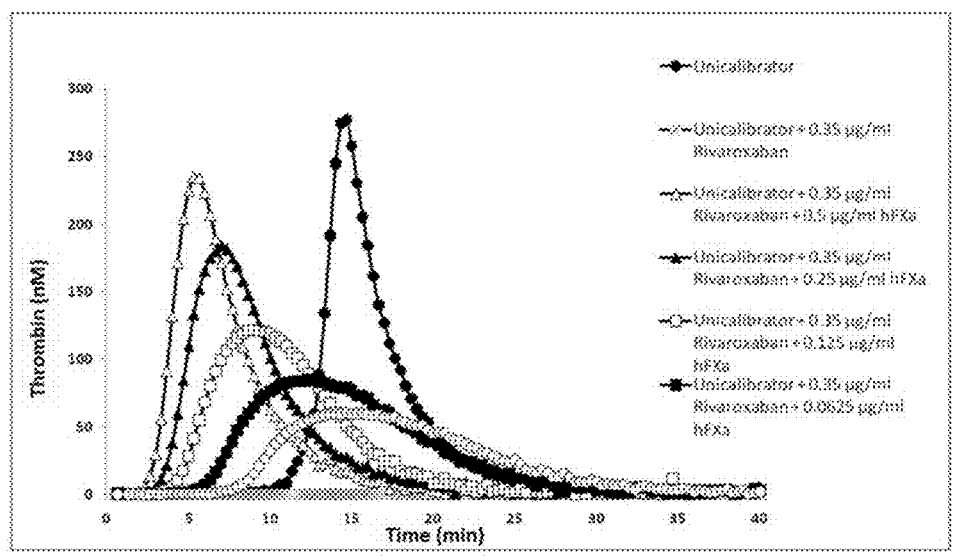

FIG. 8: Thrombinograms obtained from the addition of 0.03 to 0.5 μg/mL of activated FX to a normal plasma pool following activation with cephalin in the presence of Rivaroxaban (0.35 μg/ml):
  on the x-axis: time (in minutes)
  on the y-axis: the maximum concentration of thrombin observed (in nM)

The normal plasma pool sample without Rivaroxaban (0.35 µg/ml) is represented by the curve ●. The same plasma activated under the same conditions but in the presence of Rivaroxaban (0.35 µg/ml) is represented by the curve x. The effect of the concentrations of FXa added to normal plasma is represented by the following curves: 0.0312 µg/ml (○); 0.0625 µg/ml (■); 0.125 µg/ml (□); 0.25 µg/ml (▲) and 0.5 µg/ml (Δ).

EXAMPLES

Example 1: Extrinsic Coagulation Pathway (TF 1 pM/PL 4 µM)

1—Protocol
1.1—Reagents
Thrombin calibrator (Stago)
  TC1103
PPP reagent 5 pM (Stago)
  PPP 1009
PPP reagent low (Stago)
  PPL1101
CK-Prest (Stago)
  106025
Fluo-buffer (Stago)
  FLB1012
Fluo-substrate (Stago)
  FLS1012
Rivaroxaban at 436 µg/mL
NPP (Cryopep) A1112
human FX at 6.8 mg/mL (HTI)
  AA1108
bovine FXa at 2.15 mg/mL (Hyphen Biomed)
  110728C 1.2—Experimental Protocol The stock solution of rivaroxaban at 436 µg/mL is diluted in 5% DMSO in order to obtain intermediate concentrations which, added to the NPP (Normal Pool Plasma), give final concentrations of rivaroxaban in µg per mL of plasma.

FX or FXa are introduced into the plasma without an incubation step.

It is considered that 1 unit of FX=10 µg/mL in the plasma, corresponding to a 100% level of FX in the plasma.

The thrombin generation test consists of activating coagulation ex vivo either using a mixture of tissue factor and phospholipids, or using cephalin and then measuring the concentration of thrombin generated over time.

The thrombin generation tests are carried out on 80 µl of a plasma pool optionally containing FX and/or Rivaroxaban in the presence either of 20 µl of PPP reagent (Stago) finally containing 5 pM of Tissue Factor (TF) and 4 µM of phospholipids (PL), or in the presence of 20 µL of cephalin (CK-Prest reconstituted with 5 mL of distilled $H_2O$).

The reaction is started by the addition of 20 µL of Fluca-kit (substrate+$CaCl_2$) which constitutes the start of the measurement of the appearance of thrombin. The appearance of fluorescence is measured on a fluorometer of the Fluoroskan Ascent type (ThermoLabsystems) at an excitation wavelength of 390 nm and emission wavelength of 460 nm. The thrombinograms (curves representing the intensity of fluorescence as a function of time) are then analyzed using the Thrombinoscope™ software which converts the fluorescence value to nM of thrombin by comparative calculation.

2—Results 2.1—Effects of FX (10 µg/Ml) on a Plasma Overloaded with Rivaroxaban

All of the results are shown in Table 1 below and are illustrated by the thrombinograms of FIGS. 1-A and 1-B:

TABLE 1

Effect of factor X on a normal plasma or plasma supplemented with 0.5 µg/mL of Rivaroxaban.

| | TGT Fluoroskan (FT = 1 pM and PL = 4 µM final) | | | | | | |
|---|---|---|---|---|---|---|---|
| | FX (HTI) in µg/mL final | LT (min) | ETP (nM × min) | Peak (nM) | TTP (min) | ST (min) | mVRI (nM/min) | PT (RecombiPlastin ISI: 1.0) in seconds |
| PNP | 0 | 8 | 1190 | 127.15 | 12.33 | 38 | 29.36 | 11.9 |
|  | 10 | 6.33 | 1244 | 136.38 | 11.17 | 35.5 | 28.18 | 11.1 |
| PNP + | 0 | 25.5 | nd | 7.42 | 49.33 | nd | 0.31 | 32.5 |
| rivaroxaban at 0.5 µg/ml | 10 | 25.83 | nd | 8 | 53.67 | nd | 0.29 | 29.3 |

LT = lag time, ETP = endogenous thrombin potential, TTP = time to peak, ST = start time, mVRI = mean velocity rate index, PT = prothrombin time.

The addition of 10 µg/mL of FX to a normal plasma slightly increases (+13%) the total quantity of thrombin generated (ETP), the height of the peak (+7.3%) and reduces the period of time comprised between triggering the reaction and the point of maximum thrombin concentration (TTP) with respect to values that can be observed for a normal plasma (FIG. 1-A).

The addition of 0.5 µg/mL of Rivaroxaban completely destroys the ability to generate thrombin from normal plasma, following activation by tissue factor and phospholipids. Supplementation with 10 µg/mL of FX from a normal plasma overloaded with Rivaroxaban at 0.5 µg/mL does not make it possible to restore a thrombin generation different from that obtained during overloading with Rivaroxaban (FIG. 1-B).

In conclusion, commercial human FX (HTI) at 10 µg/mL final does not correct a plasma overloaded with rivaroxaban at 0.5 µg/mL in the extrinsic pathway at 1 pM of TF.

2.2—Effects of FX (25 µg/Ml or 100 µg/ml) on a Plasma Overloaded with Rivaroxaban (0.5 µg/ml)

All of the results are shown in Table 2 below and are illustrated by the thrombinograms of FIGS. 1-C and 1-D:

TABLE 2

Dose-effect of factor X on a normal plasma containing 0.5 μg/mL of Rivaroxaban.

| | | TGT Fluoroskan (FT = 1 pMet and PL = 4 μM final) | | | | | | |
|---|---|---|---|---|---|---|---|---|
| Names of the graphs | final concentration FX (HTI) (μg/mL) | rivaroxaban (μg/mL) | LT (min) | ETP (nM × min) | Peak (nM) | TTP (min) | ST (min) | mVRI (nM/min) |
| PNP alone | | PNP | 7.55 | 1145 | 108.42 | 12.39 | 41.5 | 22.40 |
| PNP diluted 1/2 FBS | | 0 | 7.05 | 1948 | 161.58 | 13.56 | 45.5 | 24.82 |
| Riva 0.5 μg/mL | | 0.5 | 30.59 | nd | 6.83 | 58.81 | nd | 0.24 |
| PNP + FX (HTI) 25 μg/mL | 25 | 0 | 5.55 | 1285 | 118.82 | 11.06 | 36.5 | 21.56 |
| R0.5 + FX (HTI) 25 μg/mL | | 0.5 | 29.09 | nd | 11.22 | 58.64 | nd | 0.38 |
| PNP + FX (HTI) 100 μg/mL | 100 | 0 | 5.88 | 1327 | 149.34 | 10.22 | 35.5 | 34.41 |
| R0.5 + FX (HTI) 100 μg/mL | | 0.5 | 58.31 | nd | 1.77 | 62.15 | nd | 0.46 |

LT = lag time, ETP = endogenous thrombin potential, TTP = time to peak, ST = start time, mVRI = mean velocity rate index.

The addition of FX (25 μg/ml or 100 μg/ml) to a normal plasma increases the total quantity of thrombin generated (+13 and +16% respectively), the height of the peak (+9.5% and 37% respectively) and reduces the period of time comprised between triggering the reaction and the appearance of thrombin but is incapable of reversing the effects of the Rivaroxaban.

In conclusion, commercial human FX (HTI) increases, in a dose-dependent manner, the thrombin generation of a normal plasma pool in the extrinsic pathway at 1 pM of TF final. By contrast it does not correct thrombin generation of a plasma overloaded with Rivaroxaban to 0.5 μg/mL up to concentrations of 100 μg/ml i.e. 10 U/ml.

Example 2: Intrinsic Coagulation Pathway (Cephalin Alone)

1—Protocol

The reagents, the automated equipment and the experimental protocol are identical to those described in Example 1.

The thrombin generation tests are carried out on 80 μl of a normal plasma pool optionally containing FX and/or Rivaroxaban in the presence of 20 μl of cephalin (CK-Prest reconstituted with 5 mL of distilled H$_2$O) and 20 μL fluca-kit (substrate+CaCl$_2$).

2—Results 2.1—Effect of FX on a Normal Plasma Overloaded with Rivaroxaban

All of the results are shown in Table 3 below and are illustrated by the thrombinograms of FIG. 2:

The addition of 10 μg/mL of FX to a normal plasma increases the total quantity of thrombin generated by 19%. Moreover, the addition of 10 μg/mL of FX to a normal plasma reduces the period of time comprised between triggering the reaction and the start of clot formation (LT) and the period of time comprised between triggering the reaction and the point of maximum thrombin concentration (TTP). The addition of 0.35 μg/mL of Rivaroxaban completely destroys the ability to generate thrombin from normal plasma following activation with Cephalin. The addition of 10 μg/mL of FX to a normal plasma overloaded with Rivaroxaban at 0.35 μg/mL does not make it possible to restore thrombin generation.

In conclusion, commercial human FX (HTI) at 10 μg/mL final does not correct a plasma overloaded with Rivaroxaban at 0.35 μg/mL in the intrinsic pathway.

In the intrinsic pathway, as in the extrinsic pathway, FX (HTI) does not correct a plasma overloaded with Rivaroxaban (at 0.35 μg/ml).

Example 3: Generation of Thrombin by Activation of the Extrinsic Coagulation Pathway (TF 5 pM/PL 401)

1—Protocol

The reagents, the automaton and the experimental protocol are identical to those described in Example 1.

The thrombin generation tests are carried out on 80 μl of a normal plasma pool containing FXa and/or Rivaroxababn in the presence of 20 μl of PPP reagent low finally containing 1 pM of Tissue Factor (TF) and 4 μM of phospholipids (PL), and 20 μL fluca-kit (substrate+CaCl2).

2—Results

All of the results are shown in Table 4 below and are illustrated by the thrombinograms of FIGS. 3-A and 3-B:

TABLE 3

Effect of factor X on a normal plasma containing 0.35 μg/mL of Rivaroxaban.

| | | CAT (cephalin) | | | | | |
|---|---|---|---|---|---|---|---|
| | FX (HTI) in μg/mL final | LT (min) | ETP (nM × min) | Peak (nM) | TTP (min) | ST (min) | mVRI (nM/min) |
| PNP | 0 | 22 | 1213 | 188.63 | 25.33 | 42 | 56.65 |
| | 10 | 17 | 1441 | 225.75 | 20.17 | 35.5 | 71.21 |
| PNP + rivaroxaban at 0.35 μg/ml | 0 | 48.17 | 230.5 | 8.49 | 54 | 116 | 1.46 |
| | 10 | nd | nd | nd | nd | nd | nd |

LT = lag time, ETP = endogenous thrombin potential, TTP = time to peak, ST = start time, mVRI = mean velocity rate index.

TABLE 4

Effect of factor Xa on a normal plasma containing 0.35 µg/mL of Rivaroxaban.

| | | TGT Fluoroskan (FT = 5 pM and PL = 4 µM final) | | | | | | PT (sec) with | |
|---|---|---|---|---|---|---|---|---|---|
| | | LT (min) | ETP (nM × min) | Peak (nM) | TTP (min) | ST (min) | mVRI (nM/min) | RecombiPlastin 2G (ISI: 1.0) | aPTT (sec) with PTT-A |
| PNP | 0 bovine FXa in µg/mL final | 3.83 | 1612 | 293 | 6.78 | 21.67 | 101.38 | 11.7 | 31.3 |
| PNP | 0 | 4.33 | 1782 | 297 | 7 | 23.67 | 111.24 | 11.7 | 31.3 |
| | 0.5 | 3.67 | 1762 | 299 | 6.44 | 23 | 107.94 | 11.3 | 23.1 |
| | 1 | 3 | 1725 | 315.2 | 5.67 | 21.67 | 118.05 | 10.8 | 20.6 |
| | 1.5 | 2.67 | 1708 | 332.69 | 5.22 | 20 | 130.47 | 10.6 | 20.4 |
| | 2 | 2.89 | 1873 | 322 | 5.44 | 22.67 | 126.27 | 10.4 | 19.6 |
| | 2.5 | 2.67 | 1929 | 330.37 | 5.22 | 22.67 | 129.56 | 10.2 | 19.3 |
| | 5 | 2.33 | 2033 | 353.39 | 4.67 | 21.67 | 151.02 | 9 | 17.1 |
| PNP + rivaroxaban at 0.35 µg/mL | 0 | 11.11 | 772 | 31.32 | 25.33 | 67 | 2.20 | 26 | 50.5 |
| | 0.5 | 6.78 | 1513 | 155.96 | 11.33 | 31.33 | 34.28 | 25.8 | 21 |
| | 1 | 6.33 | 1577 | 192.53 | 10.22 | 28.33 | 49.49 | 24.8 | 19.1 |
| | 1.5 | 5.56 | 1500.67 | 211.74 | 9 | 25.33 | 61.55 | 24.8 | 19.3 |
| | 2 | 5.67 | 1490.67 | 199.24 | 9.33 | 26.67 | 54.44 | 24.4 | 16.9 |
| | 2.5 | 5.67 | 1548 | 199.81 | 9.44 | 26.67 | 53.00 | 25 | 18.5 |
| | 5 | 5 | 1549 | 208.59 | 8.78 | 25.67 | 55.18 | 22.6 | 14.8 |

LT = lag time, ETP = endogenous thrombin potential, TTP = time to peak, ST = start time, mVRI = mean velocity rate index, PT = prothrombin time, aPTT = activated partial thromboplastin time, PTT-A = activated prothromboplastin.

The addition of FXa to a normal plasma reduces the period of time comprised between triggering the reaction by successive stages in a dose-dependent manner. By contrast, the addition of 0.35 µg/mL of rivaroxaban to a normal plasma increases this period of time by a factor comprised between 2 and 3 and completely eliminates the formation of thrombin (FIGS. 3-A and 3-B).

The addition of FXa to the normal plasma reduces the period of time comprised between triggering the reaction and the point of maximum thrombin concentration (TTP) by successive stages in a dose-dependent manner. By contrast, the addition of 0.35 µg/mL of rivaroxaban to a normal plasma increases this period of time by a factor comprised between 3 and 4.

The addition of FXa to the normal plasma increases by approximately 14% the total quantity of thrombin generated (ETP) for the highest dose of FXa (5 µg/mL). By contrast, the addition of 0.35 µg/mL of rivaroxaban to a normal plasma reduces the total quantity of thrombin generated.

The addition of increasing quantities of FXa to a normal plasma overloaded with Rivaroxaban at 0.35 µg/mL restores the two parameters LT and ETP to the level observed for normal plasma alone.

FXa at 0.5 to 5 µg/mL final partially corrects a plasma overloaded with Rivaroxaban at 0.35 µg/mL in a dose-dependent manner up to 2.5 µg/mL in the extrinsic pathway, at 5 pM of TF. Factor Xa also improves thrombin generation from a normal plasma pool in a dose-dependent manner.

In conclusion, it is noted that the addition of FXa to a normal plasma appears to provide a moderate thrombogenic effect by allowing the generation of larger quantities of thrombin earlier than those obtained from a non-supplemented plasma. On the other hand, the inhibitory effect of Rivaroxaban at 0.35 µg/ml is largely eliminated by the addition of FXa with a plateau effect at 2.5 µg/ml which does not however make it possible to achieve the thrombin values generated in normal plasma.

Example 4: Assessment of the Useful Doses of Factor Xa (FXa) Inducing Coagulation or Required to Counterbalance the Effect of Rivaroxaban 1—Induction of Thrombin Generation by Factor Xa Alone The effect of an overdose of FXa in a normal plasma was assessed by measuring thrombin generation (TGT) without additional induction of coagulation (FIG. 4). Doses from 0.01 µg/ml to 1 µg/ml of FXa were compared. The quantity of thrombin generated depends on the dose of FXa added. The effect of FXa was compared to normal plasma without induction of coagulation (●), activated by tissue factor (X) or cephalin (◇). The doses of FXa from 0.01 µg/ml to 0.05 µg/ml produce quantities of thrombin similar to that of a normal plasma activated by TF or cephalin and follow the same appearance kinetics. These results suggest that under these experimental conditions, FXa at a dose of 50 µg/ml should not be thrombogenic. The dose of 50 ng/ml would therefore correspond to the lowest useable dose of FXa making it possible to restore coagulation.

2—Induction of Thrombin Generation by Tissue Factor

The effect of an overdose of FXa in normal plasma was assessed by measuring thrombin generation (TGT) following induction by tissue factor (0.5 pM) (FIG. 5, Table I). Doses of 0.03 µg/ml to 0.5 µg/ml of FXa were compared. The quantity of thrombin generated depends on the dose of FXa added. Doses of FXa from 0.03 µg/ml to 0.125 µg/ml produce quantities of thrombin similar to that of an activated normal plasma (●) and follow the same appearance kinetics. These results suggest that under these experimental conditions, FXa does not appear to induce thrombogenicity additional to that provided by the inducer in the case of doses from 0.03 µg/ml to 0.125 µg/ml.

A similar experiment was repeated in the presence of a therapeutic dose of 0.35 µg/ml of Rivaroxaban (FIG. 6, Table I). The dose of Rivaroxaban used reduces thrombin generation very significantly (approximately 75%; curve x) compared with that obtained in an untreated plasma (●). FXa supplementation of 0.03 µg/ml (○) does not make it possible to recover significant thrombin generation. On the other hand, a correction of thrombin generation is obtained starting from 0.06 µg/ml (■) up to a dose of 0.25 µg/ml (▲). In the case of the higher dose, the quantity of thrombin generated exceeds that of the control suggesting an FXa overdose and therefore a possible thrombogenic effect despite the Rivaroxaban.

TABLE I

Values of lag time, thrombin potential, peak height and time to peak thrombin generation induced by tissue factor in a normal plasma in the presence or absence of factor Xa and/or Rivaroxaban (data extracted from FIGS. 4 and 5).

| Name of group | Lag time (min) | ETP (nM) | Peak (nM) | ttPeak (min) |
|---|---|---|---|---|
| Unicalibrator | 3.83 | 1179 | 123.96 | 8.33 |
| Unicalibrator + 0.5 µg/ml hFXa | 1.67 | 1462 | 211.77 | 5.33 |
| Unicalibrator + 0.25 µg/ml hFXa | 2.33 | 1339 | 172.05 | 6.33 |
| Unicalibrator + 0.125 µg/ml hFXa | 2.67 | 1238.5 | 146.77 | 7 |
| Unicalibrator + 0.0625 µg/ml hFXa | 3 | 1189.5 | 134.13 | 7.33 |
| Unicalibrator + 0.03125 µg/ml hFXa | 3.33 | 1147.5 | 119.98 | 8 |
| Unicalibrator + 0.35 µg/ml Rivaroxaban | 10.17 | 282 | 10.69 | 20.5 |
| Unicalibrator + 0.35 µg/ml Rivaroxaban + 0.5 µg/ml hFXa | 2.67 | 1368.5 | 165.27 | 6.33 |
| Unicalibrator + 0.35 µg/ml Rivaroxaban + 0.25 µg/ml hFXa | 3 | 1317.5 | 127.63 | 7.67 |
| Unicalibrator + 0.35 µg/ml Rivaroxaban + 0.125 µg/ml hFXa | 3.33 | 1217.5 | 88.16 | 9.67 |
| Unicalibrator + 0.35 µg/ml Rivaroxaban + 0.0625 µg/ml hFXa | 3.83 | 1189.5 | 73.14 | 10.83 |
| Unicalibrator + 0.35 µg/ml Rivaroxaban + 0.03125 µg/ml hFXa | 4 | 712 | 28.83 | 14.5 |

3—Induction of Thrombin Generation by Cephalin

A series of similar experiments is carried out by inducing the initiation of coagulation by cephalin. The series of preliminary experiments mimics the extrinsic activation of coagulation. This second series of experiments mimics the intrinsic activation of coagulation. The presence of FXa in an increasing quantity in normal plasma (●) reduces the speed of appearance of thrombin without changing the total quantity of thrombin generated (FIG. 7, Table II). The speed of appearance of the thrombin is correlated with the dose of FXa added. Shorter times to peak are obtained in the presence of FXa. This difference is significant and suggests a risk of thrombosis starting from 0.25 µg/ml of FXa.

The effect of FXa following the induction of thrombin generation by cephalin is then measured in the presence of Rivaroxaban at 0.35 µg/ml (FIG. 8, Table II). The Rivaroxaban completely inhibits thrombin generation induced by cephalin (curve x). The presence of FXa in an increasing concentration makes it possible to increase the quantity of thrombin generated in a dose-dependent manner, as well as to reduce the time to peak. A maximum quantity of thrombin is obtained in the case of a concentration comprised between 0.125 and 0.25 µg/ml.

TABLE II

Values of lag time, thrombin potential, peak height and time to peak of thrombin generation induced by the cephalin of a normal plasma in the presence or absence of factor Xa and/or rivaroxaban (data extracted from FIGS. 7 and 8).

| Name of group | Lag time (min) | ETP (nM) | Peak (nM) | ttPeak (min) |
|---|---|---|---|---|
| Unicalibrator | 12.33 | 1277.5 | 283.42 | 14.67 |
| Unicalibrator + 0.5 µg/ml hFXa | 3.67 | 1291 | 283.25 | 6 |
| Unicalibrator + 0.25 µg/ml hFXa | 5.83 | 1234.5 | 287.96 | 7.83 |
| Unicalibrator + 0.125 µg/ml hFXa | 8.5 | 1229 | 297.26 | 10.33 |
| Unicalibrator + 0.0625 µg/ml hFXa | 10 | 1233 | 285.93 | 12 |
| Unicalibrator + 0.03125 µg/ml hFXa | 10.67 | 1225 | 272.54 | 13.17 |
| Unicalibrator + 0.35 µg/ml Rivaroxaban | 0 | 0 | 0 | 0 |
| Unicalibrator + 0.35 µg/ml Rivaroxaban + 0.5 µg/ml hFXa | 3 | 1232.5 | 235.61 | 5.5 |
| Unicalibrator + 0.35 µg/ml Rivaroxaban + 0.25 µg/ml hFXa | 3.67 | 1221.5 | 183.27 | 7.17 |
| Unicalibrator + 0.35 µg/ml Rivaroxaban + 0.125 µg/ml hFXa | 4.83 | 1079 | 121.62 | 9.33 |
| Unicalibrator + 0.35 µg/ml Rivaroxaban + 0.0625 µg/ml hFXa | 6.33 | 1060.5 | 84.19 | 12.17 |
| Unicalibrator + 0.35 µg/ml Rivaroxaban + 0.03125 µg/ml hFXa | 8.33 | 867.5 | 59.78 | 15 |

In conclusion, the data presented show that FXa has the possibility of correcting the presence of Rivaroxaban in normal plasma following the induction of the intrinsic pathway by cephalin or of the extrinsic pathway by tissue factor. For doses less than or equal to 0.25 µg/ml of factor Xa and in the case of a dose of Rivaroxaban of 0.35 µg/ml, the data obtained in terms of TGT do not identify a major risk of thrombogenicity. In the case of doses greater than 0.25 µg/ml, thrombin generation time is very short and could reveal a thrombogenic risk.

The invention claimed is:

1. A method of treating in a patient of haemorrhagic events induced by taking anticoagulants comprising administering to a patient in need thereof an effective amount of factor Xa having a procoagulant activity due to a prothrombin activation.

2. The method according to claim 1, in which the anticoagulants are low-molecular-weight heparins.

3. The method according to claim 2, in which the low-molecular-weight heparins are selected from bemiparin, certoparin, deltaparin, enoxaparin, nadroparin, parnaparin, reviparin or tinzaparin.

4. The method according to claim 1, in which the anticoagulants are specific inhibitors of factor Xa.

5. The method according to claim 4, in which the specific inhibitors of factor Xa are selected from apixaban, betrixaban, edoxaban, otamixaban or rivaroxaban.

6. The method according to claim 1, in which the anticoagulants are the oligosaccharides fondaparinux or idraparinux.

7. The method according to claim 1, in which factor Xa restores procoagulant activity without the latter exceeding the basal level of the procoagulant activity measured in a group of healthy patients.

8. The method according to claim 1, in which factor Xa is a native protein isolated from plasma or a recombinant protein.

9. The method according to claim 1, in which factor Xa has an increased circulating half-life compared with native factor Xa isolated from plasma.

10. The method according to claim 1, in which said patient is a human being or an animal.

11. A method for treating haemorrhagic events induced by taking anticoagulants, in a mammal, comprising a step of administration of factor Xa having a procoagulant activity due to a prothrombin activation to said mammal in a sufficient quantity making it possible to restore basal procoagulant activity.

12. The method according to claim 11, in which the anticoagulants are specific inhibitors of factor Xa.

13. The method according to claim 12, in which the specific inhibitors of factor Xa are selected from apixaban, betrixaban, edoxaban, otamixaban or rivaroxaban.

14. The method according to claim 13, in which factor Xa is administered to the mammal during or after taking specific inhibitors of factor Xa.

15. The method according to claim 14, in which factor Xa is administrated to human.

16. The method according to claim 11, in which said mammal is human.

* * * * *